United States Patent
Duffy et al.

(10) Patent No.: US 12,112,740 B2
(45) Date of Patent: Oct. 8, 2024

(54) CREATIVE WORK SYSTEMS AND METHODS THEREOF

(71) Applicant: SOCIETE BIC, Clichy (FR)

(72) Inventors: David Duffy, Clichy (FR); Bernadette Elliott-Bowman, Clichy (FR)

(73) Assignee: SOCIÉTÉ BIC, Clichy (FR)

( * ) Notice: Subject to any disclaimer, the term of this patent is extended or adjusted under 35 U.S.C. 154(b) by 359 days.

(21) Appl. No.: 17/545,815

(22) Filed: Dec. 8, 2021

(65) Prior Publication Data
US 2022/0230626 A1 Jul. 21, 2022

(30) Foreign Application Priority Data

Jan. 21, 2021 (EP) ..................................... 21305072

(51) Int. Cl.
*G10L 15/01* (2013.01)
*G10L 13/027* (2013.01)
(Continued)

(52) U.S. Cl.
CPC ............ *G10L 15/01* (2013.01); *G10L 13/027* (2013.01); *G10L 15/02* (2013.01); *G10L 15/16* (2013.01);
(Continued)

(58) Field of Classification Search
CPC ....... G10L 15/01; G10L 13/027; G10L 15/02; G10L 15/16; G10L 15/26;
(Continued)

(56) References Cited

U.S. PATENT DOCUMENTS

| | | | |
|---|---|---|---|
| 2007/0288230 A1* | 12/2007 | Datta | G06F 40/126 707/E17.073 |
| 2011/0207099 A1* | 8/2011 | Chen | A61B 5/7264 434/236 |

(Continued)

OTHER PUBLICATIONS

Khawaja, M. Asif, et al. "Potential speech features for cognitive load measurement." Proceedings of the 19th Australasian conference on computer-human interaction: Entertaining user interfaces. 2007, pp. 57-60 (Year: 2007).*

(Continued)

*Primary Examiner* — Jesse S Pullias
*Assistant Examiner* — Michael C. Lee
(74) *Attorney, Agent, or Firm* — Bookoff McAndrews, PLLC

(57) ABSTRACT

A computer-implemented method for measuring cognitive load of a user creating a creative work in a creative work system, may include generating at least one verbal statement capable of provoking at least one verbal response from the user, prompting the user to vocally interact with the creative work system by vocalizing the at least one generated verbal statement to the user via an audio interface of the creative work system, and obtaining the at least one verbal response from the user via the audio interface, and determining the cognitive load of the user based on the at least one verbal response obtained from the user, wherein generating the at least one verbal statement is based on at least one predicted verbal response suitable for determining the cognitive load of the user.

20 Claims, 7 Drawing Sheets

(51) Int. Cl.
  *G10L 15/02* (2006.01)
  *G10L 15/16* (2006.01)
  *G10L 15/26* (2006.01)

(52) U.S. Cl.
  CPC ........ *G10L 15/26* (2013.01); *G10L 2015/025* (2013.01); *G10L 2015/027* (2013.01)

(58) Field of Classification Search
  CPC ......... G10L 2015/025; G10L 2015/027; G10L 25/66; G10L 15/22; A61B 5/4803; G16H 50/30
  See application file for complete search history.

(56) References Cited

U.S. PATENT DOCUMENTS

| | | | |
|---|---|---|---|
| 2016/0372138 A1 | 12/2016 | Shinkai et al. | |
| 2019/0034157 A1* | 1/2019 | Steinberg | G06F 3/165 |
| 2019/0175090 A1* | 6/2019 | Reiner | A61B 5/165 |
| 2019/0287520 A1* | 9/2019 | Lee | G10L 15/22 |
| 2019/0362717 A1* | 11/2019 | Koga | G10L 15/22 |
| 2020/0365275 A1* | 11/2020 | Barnett | A61B 5/4803 |
| 2020/0388287 A1* | 12/2020 | Anushiravani | A61B 5/0823 |

OTHER PUBLICATIONS

Yin, Bo, et al. "Investigating speech features and automatic measurement of cognitive load." 2008 IEEE 10th Workshop on Multimedia Signal Processing. IEEE, 2008, pp. 1-6. (Year: 2008).*

Chen, Fang, et al. "Multimodal behavior and interaction as indicators of cognitive load." ACM Transactions on Interactive Intelligent Systems (TiiS) 2.4 (2012), pp. 1-36 (Year: 2012).*

Vukovic, Maria, et al. "Estimating cognitive load from speech gathered in a complex real-life training exercise." International Journal of Human-Computer Studies 124 (2019): pp. 116-133 (Year: 2019).*

Extended European Search Report issued on Jul. 2, 2021 in counterpart European Patent Application No. 21305072.7 (11 pages, in English).

Quatieri, T. F. et al. "Vocal biomarkers to discriminate cognitive load in a working memory task", Sep. 6, 2015 (5 pages, in English).

* cited by examiner

CREATIVE WORK SYSTEMS AND METHODS THEREOF

CROSS REFERENCE TO RELATED APPLICATIONS

This application claims priority from European patent application No. 21305072.7, filed on Jan. 21, 2021, the contents of which are hereby incorporated herein in their entirety by this reference.

TECHNICAL FIELD

This specification relates to a computer-implemented method for measuring cognitive load of a user creating a creative work in a creative work system, and to a creative work system for measuring cognitive load of a user creating a creative work.

BACKGROUND

Cognitive load is a measure of the cognitive effort a human being is putting into her or his current activity or task. It is based on the amount of working memory resources in the brain being used. Users with a higher cognitive load may find it challenging to produce creative work, this problem is intensified for users with limited experience or young users, e.g., children. Service providers face significant technical difficulties in determining the cognitive load of the users while they are producing creative work.

Recent research shows that the cognitive load of an individual can be learnt from analyzing vocal features in her or his speech. In fact, the properties of speech features such as phonemes, pitch variations, and pseudo-syllables can be used to determine the current cognitive load of the speaker. Furthermore, the cognitive load can also be determined by analyzing a video sequence (e.g. based on eye tracking) of the individual.

Creative activities may lead to increased cognitive load of the creator. It is known that positive feedback to creative tasks can reduce the cognitive load of the creator.

SUMMARY

According to a first aspect, there is provided a computer-implemented method for measuring cognitive load of a user creating a creative work in a creative work system. The method comprises generating at least one verbal statement capable of provoking at least one verbal response from the user. The method further comprises prompting the user to vocally interact with the creative work system by vocalizing the at least one generated verbal statement to the user via an audio interface of the creative work system. The method further comprises obtaining the at least one verbal response from the user via the audio interface. The method further comprises determining the cognitive load of the user based on the at least one verbal response obtained from the user. Generating the at least one verbal statement is based on at least one predicted verbal response suitable for determining the cognitive load of the user.

According to a second aspect, there is provided a creative work system for measuring cognitive load of a user creating a creative work. The creative work system comprises a user interface comprising an audio interface. The creative work system is configured to run the method according to the first aspect (or an embodiment thereof).

Dependent embodiments of the aforementioned aspects are given in the dependent claims and explained in the following description, to which the reader should now refer.

The method of the first aspect (or an embodiment thereof) and the corresponding creative work system of the second aspect (or an embodiment thereof) are directed towards engaging an individual (viz. a creator or user) creating a creative work to vocally interact with the creative work system and, as an example, towards providing feedback (i.e. tailored responses), in particular positive or useful feedback, to the individual based on the cognitive load measured by analyzing the speech of the individual.

Measuring cognitive load can be used to assist the user of the creative work system with creating the creative work. Such may be conducive to engaging the user with the creative work or task and to reducing frustration. As an example, an (infant) user (e.g. a pupil or student) may be guided through creating the creative work system. In cases, where currently measured cognitive load is rather high, the creative work system may try to alleviate the current task (e.g. drawing an apple) for the (infant) user by applying means known in cognitive psychology (e.g. giving encouragement or praise). This can be used for autodidactic learners or when supervision (e.g. a teacher) is out of reach, the latter a circumstance typically encountered during homework and/or silent study sessions. In particular, when further applying state-of-the-art artificial intelligence algorithms capable of acquiring at least a basic understanding of the semantics of the user's speech and/or visually capturing (e.g. using a camera) and interpreting the creative work as it progresses, the creative work system can be used to supervise the user online. As an example, in case, the creative work system figures out that the (infant) user has a hard time drawing an apple it may offer a picture of an apple or a video tutorial on how to draw an apple. Hence, the creative work system equipped with the method of the first aspect can be used in self-study, teaching and/or education.

Conventionally or often, a creative work is assessed or evaluated largely based on a final state the creative work is in after its completion. Additionally, some more outer factors such as a duration of creating the creative work can be taken into account. On the other hand, recording the cognitive load, and e.g. the corresponding contemporaneous features, as the creation of the creative work progresses can be beneficial in that the record provides a handle to analyze the creative work even after its completion. Again, such can be used in self-study, teaching and/or education. As an example, a teacher may not have the time to supervise all pupils at once. On the other hand, if need be, the teacher may resort to the record corresponding to the creative work of a pupil in order to assist the pupil on how make an improvement next time.

The method of the first aspect (or an embodiment thereof) comprises generating verbal statements capable of provoking verbal (i.e. can be vocalized by a speaker or a human being) responses from the user that are likely to be rich in information relevant and useful for determining the cognitive load. Such likelihoods are computed based on one or more candidate verbal statements and corresponding predicted verbal responses. In so doing, the measurement of cognitive load can be improved. In addition, vocalized verbal responses are less likely to bore the user, again reducing frustration and increasing engagement of the user.

The creative work may comprise or be an artwork, as an example, a visual artwork. An artwork is an artistic creation of aesthetic value and/or beauty. A visual artwork refers to or comprises an artwork that is visible (e.g. to human beings)

and/or tangible, or that features one or more physical forms of visual art. A visual artwork refers to or comprises visual fine art, decorative art and/or applied art. However, aesthetic value and/or beauty may be relative in that what an artwork is may e.g. depend on the user, in particular on his or her age. As an example, a child may want to be guided through realistically drawing a rather difficult object, such as e.g. an elephant. On the other hand, as another example, a non-infant (tutorial user) may be more interested in painting a holiday picture or a still life in terms of a well-known artistic style (such as e.g. neoclassicism, impressionism, expressionism, cubism, surrealism, . . . ). The visual artwork may comprise or be a painting. Alternatively, or in addition, the visual artwork may comprise or be a drawing. Alternatively, or in addition, the visual artwork may comprise or be a handwriting, in particular (a) calligraphy. Alternatively, the visual artwork may comprise or be a 3D object. In fact, the 3D object may e.g. comprise or be a sculpture (e.g. of clay, wood, or stone) or a handicraft work (e.g. of paper or cardboard). Alternatively, or in addition, the artwork may comprise a non-visual artwork or an artwork where the visual aspect is subordinate. Such an artwork may comprise or be a musical composition or rehearsing a piece of music. Alternatively, or in addition, the artwork may comprise writing poetry (e.g. a poem, figuring out how hard it was to find certain rhymes) or prose (e.g. a short story or novel).

The creative work must not comprise an artwork. Instead, the creative work may be intellectual. The creative work may comprise or be a writing task. Alternatively, or in addition the creative work may comprise or consist in inventing a concept/scheme or developing a solution to a problem.

Embodiments without a camera (apart from being cheaper) may be perceived by a user as less invasive in terms of privacy.

FIGURE DESCRIPTION

FIG. 1a schematically illustrates a computer-implemented method according to the first aspect (or an embodiment thereof) for measuring cognitive load of a user creating a creative work in a creative work system.

FIG. 1b schematically illustrates an embodiment of the computer-implemented method according to the first aspect for measuring cognitive load of a user creating a creative work in a creative work system.

FIG. 2a schematically illustrates an embodiment of the computer-implemented method according to the first aspect for measuring cognitive load of a user creating a creative work in a creative work system.

FIG. 2b schematically illustrates an embodiment of the computer-implemented method according to the first aspect for measuring cognitive load of a user creating a creative work in a creative work system.

FIG. 3 schematically illustrates a creative work system for measuring cognitive load of a user creating a creative work according to the second aspect (or an embodiment thereof).

DETAILED DESCRIPTION

Implementations described herein take advantage of modern technology infrastructure to measure the semantics of a user's speech to determine the cognitive load of a user. For example, the present disclosure leverages a machine learning model to automatically determine that a cognitive load is high for the user, e.g., based upon a verbal response of the user, and may try to alleviate the current task of the user by providing supervision. Such process of simply analyzing the vocal features to determine the current cognitive load of the users reduces the amount of computing resources used.

Figure 4A:
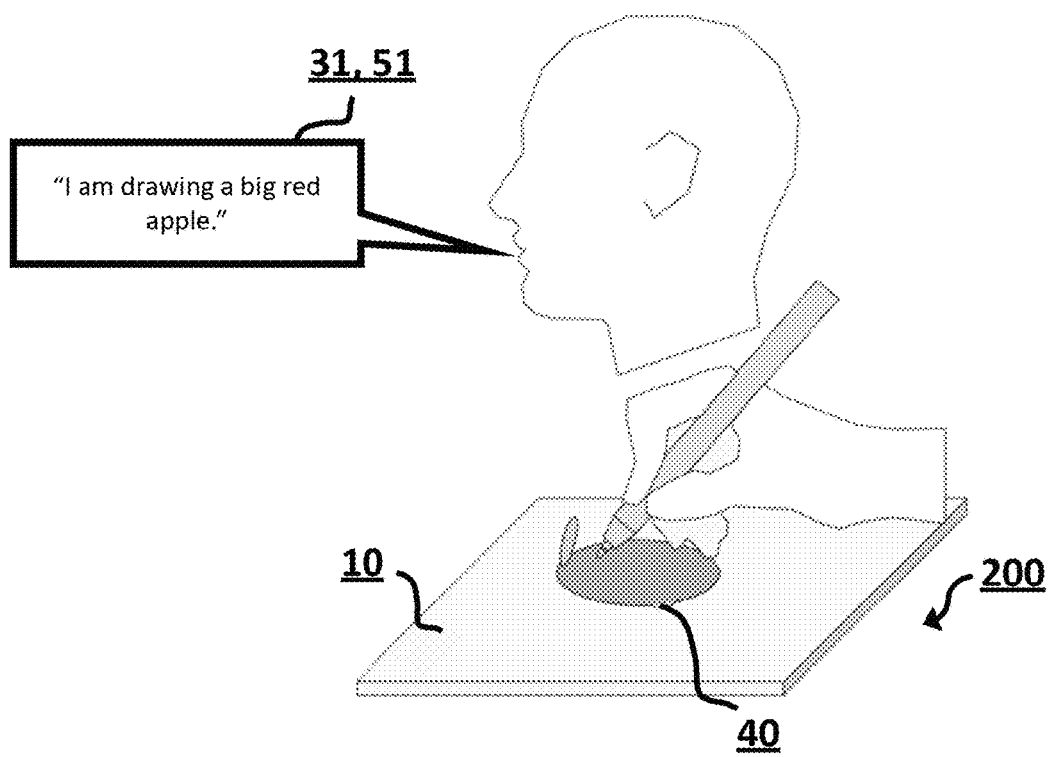
FIG. 4a illustrates creating a creative work in a creative work system.
Figure 4B:
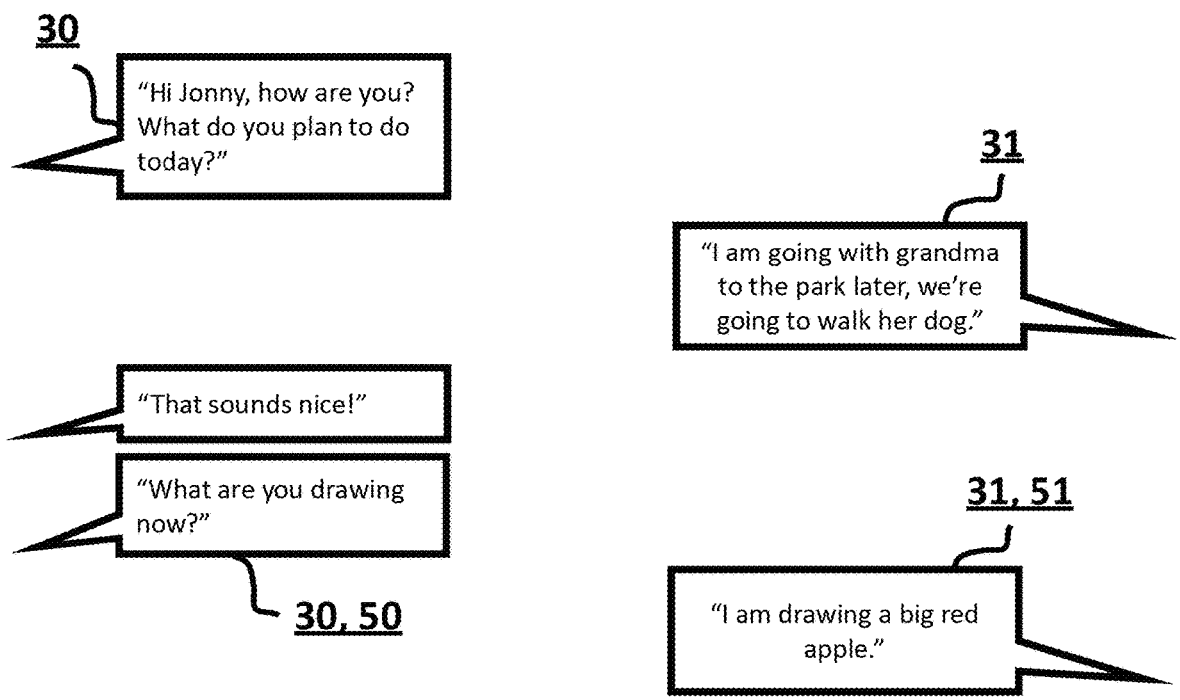
FIG. 4b illustrates an example dialogue according to the computer-implemented method of the first aspect (or an embodiment thereof).

The method 100 of the first aspect (or an embodiment thereof) and the corresponding creative work system 200 of the second aspect (or an embodiment thereof) are directed towards engaging 30, 50 a user creating a creative work 10 to vocally interact 31, 51 with the creative work system 200. As an example, and as illustrated in FIG. 4a-b, the creative work 10 may consist in drawing an apple 40 on a sheet of paper. The method may also provide feedback (i.e. tailored responses), in particular positive or useful feedback, to the user based on the cognitive load 20 measured by analyzing the speech of the individual. FIG. 4b illustrates an example dialogue aimed at engaging the user to vocally interact in order to measure her or his cognitive load 20 and have her or him reveal what she or he is currently drawing (the apple, a contemporaneous feature 40).

Figure 5A:
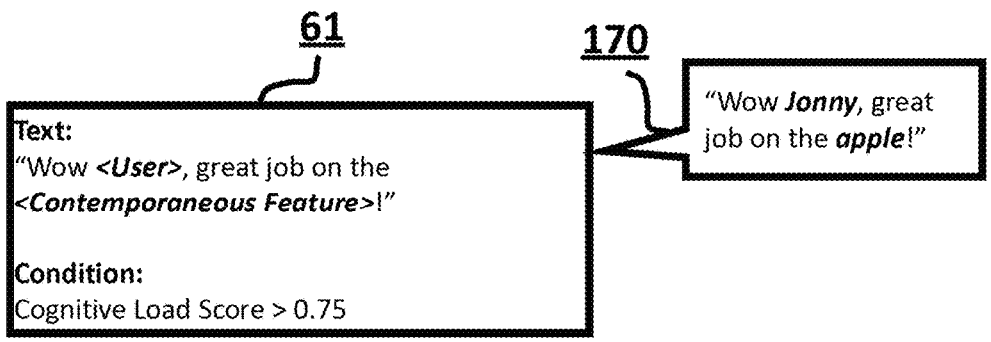
FIG. 5a illustrates an example of a tailored response based on cognitive load and a contemporaneous feature.

FIG. 5a illustrates an example of a tailored response based on the cognitive load 20 and the contemporaneous feature 40 (the apple). Note that the method may further be configured to elicit (e.g. by asking "What's your name?" and analyzing the corresponding response) and use the name of the user (Jonny).

Figure 5B:
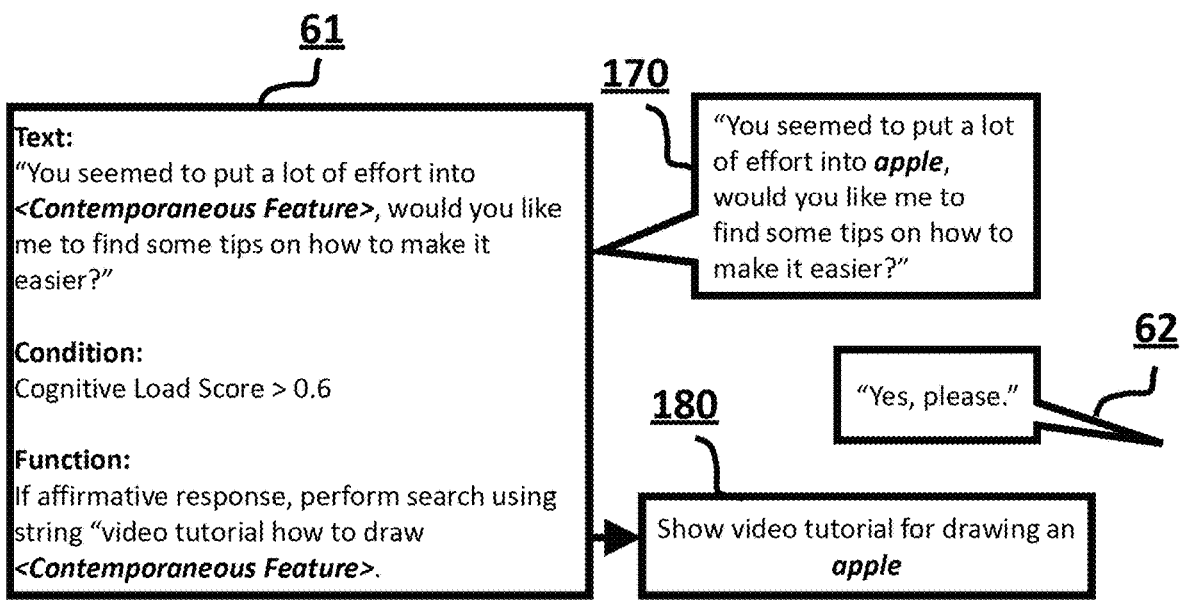
FIG. 5b illustrates an example of a tailored response provoking a third response from the user and running a third response algorithm based on the third response from the user feeding back information related to cognitive load and a corresponding contemporaneous feature.

FIG. 5b illustrates another example of a tailored response 60 provoking (e.g. offering a video tutorial on how to draw an apple) a third response 62 ("Yes, please.") from the user and running a third response algorithm based on the third response 62 from the user feeding back 180 information related to the cognitive load 20 and a corresponding contemporaneous feature 40.

Figure 5C:
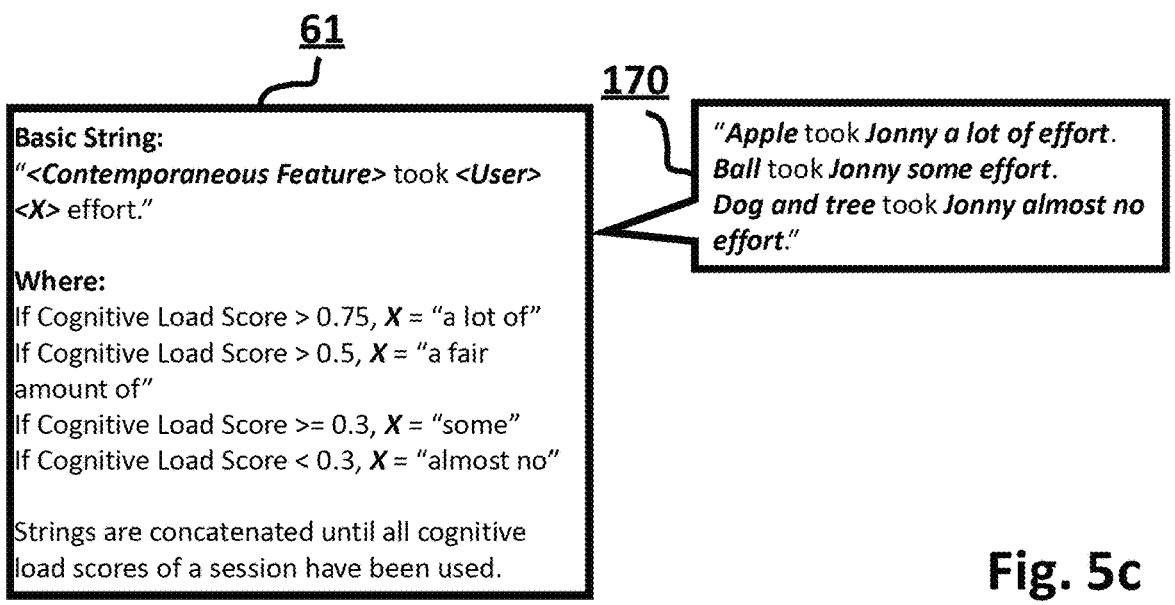
FIG. 5c illustrates an example of a tailored response comprising a record (e.g. after completion of the creative work) for more than one cognitive load and corresponding contemporaneous features.

FIG. 5c illustrates yet another example of a tailored response 60 comprising a record or a report (e.g. after completion of the creative work 10) for more than one cognitive load and corresponding contemporaneous features.

The computer-implemented method 100 for measuring cognitive load 20 (or mental effort) of the user creating a creative work 10 in a creative work system 200, comprises generating 110 at least one verbal statement 30 capable of provoking at least one verbal response 31 from the user. The method 100 further comprises prompting 120 the user to vocally interact with the creative work system by vocalizing 121 the at least one generated verbal statement 30 to the user via an audio interface 211 of the creative work system. The method 100 further comprises obtaining 130 the at least one verbal response 31 from the user via the audio interface. The method further comprises determining 140 the cognitive load 20 of the user based on the at least one verbal response 31 obtained from the user. Generating 110 the at least one verbal statement 30 is based on at least one predicted verbal response 32 suitable for determining the cognitive load 20 of the user. The computer-implemented method 100 is schematically illustrated in FIGS. 1a, 1b, 2a, and 2b.

The method 100 may further comprise determining 150 (the) at least one contemporaneous feature 40 of the creative work 10 based on the at least one obtained verbal response 31 from the user.

Alternatively, or in addition the method 100 may further comprise generating 151 at least one further verbal statement 50 capable of provoking at least one further verbal response 51 from the user. The method 100 may further comprise prompting 152 the user to vocally interact with the creative work system 200 by vocalizing 153 the at least one generated further verbal statement 50 to the user via an audio interface 211 of the creative work system. The method 100 may further comprise obtaining 154 at least one further verbal response 51 from the user via the audio interface. The method 100 may further comprise determining 155 at least one contemporaneous feature 40 of the creative work 10 based on the at least one obtained further verbal response 51 from the user. In addition, the at least one further verbal response 51 from the user may also be used for determining cognitive load 10.

Any response 31 from the user may be used to determine cognitive load 20 and/or to determine the contemporaneous feature 40.

A verbal response 31 from the user, a further verbal response 51 from the user, and/or a third response 62 (see below) from the user may comprise e.g. grunting or groaning as such is conducive to determining cognitive load. A verbal response 31 from the user, a further verbal response 51 from the user, and/or a third response 62 (see below) from the user may be spoken language comprising a text that is mostly (e.g. apart from grunting or groaning) semantically and/or linguistically interpretable with respect to at least one communication language (e.g. a natural language or an artificial language). Spoken language of the user is captured via an audio interface 211 of the creative work system 200 comprising at least one microphone 212 and at least one speaker 213.

Vocalizing 121 the at least one generated verbal statement 30, the at least one further generated verbal statement 50, and/or at least one tailored response 60 to the user via the audio interface 211 of the creative work system 200 may comprise synthesizing at least one audio signal representing the at least one generated verbal statement 30, the at least one further generated verbal statement 50, and/or at least one tailored response 60. It may further comprise playing the at least one audio signal on the audio interface of the creative work system 200. Synthesizing may comprise applying a state-of-the-art algorithm for text-to-audio conversion.

Rather than or in addition to vocalizing the at least one generated (further) verbal statement via the at least one speaker 213, the at least one generated verbal statement 30, the at least one further generated verbal statement 50, and/or at least one tailored response 60 may also be outputted on a graphical interface 214 of the creative work system 200.

The at least one contemporaneous feature 40 of the creative work 10 may comprise at least one feature (e.g. an apple) of the creative work 10 the user of the creative work system 200 has just (e.g. seconds ago) completed, or is currently working on, or is going to work on next. Such may depend on the type of question that is asked to identify the contemporaneous feature. In case of the example in FIG. 4b, the question "What are you drawing now?" is likely to be answered with a contemporaneous feature 40 the user is currently working on. Such a feature may also be referred to as a current feature. On the other hand, the term "contemporaneous" may also account for small periods of times before starting to work on a feature or after completing the feature. The at least one feature of the creative work 10 may comprise one or more of a part of the creative work, an object (e.g. apple) featured by the creative work, and an aspect of the creative work the user of the creative work can vocally refer to, name, describe, and/or specify. As creation of the creative work 10 progresses, one or more contemporaneous features 40 may be recorded, see FIG. 5c.

Generating 110 the at least one verbal statement 30 capable of provoking the at least one verbal response 31 from the user may comprise applying a candidate verbal statement algorithm configured to generate one or more candidate verbal statements, e.g. based on one or more candidate primitives queried from a candidate primitives database 220. A candidate primitive may be a parametrizable text template. Checking more than one candidate verbal statements can be used for choosing a (generated) verbal statement that is best suited for cognitive load determination.

Generating 110 the at least one verbal statement 30 capable of provoking the at least one verbal response 31 from the user may further comprise applying a conversation algorithm configured to generate for each candidate verbal statement one or more predicted verbal responses 32 and corresponding (i.e. a response probability for each predicted verbal response 32) one or more response probabilities, thereby generating, for each candidate verbal statement, a list of predicted verbal responses and a vector of response probabilities RPV. The conversation algorithm may be identical to a common predictive communication algorithm, deployed in voice interfaces or predictive text. In fact, such sequence-to-sequence models can be trained on entire sequences of text, which in this case will be a set of question sequences, each of which correspond to a set of answer sequences (Q&A language model). The weighting (or the parameters) used in the machine learn model (e.g. a neural network) can be adjusted to ensure that for a given training question input, its output is identical (or close to) the actual training answer. When the model is then used on a new question it has never seen before, it is capable of generalizing, thereby outputting a set of generated answers, each with a confidence value. The confidence value in this case can be used as a measure of probability that this is the "correct" answer, given its training data. The Q&A language model may generically be trained on human language (e.g. GTP-3) or additionally be trained on the language specific users (e.g. voices of children or for particular languages).

Generating 110 the at least one verbal statement 30 capable of provoking the at least one verbal response 31 from the user may further comprise applying a predicted verbal response assessment algorithm configured to assign a response score to each predicted verbal response 32, thereby generating, for each candidate verbal statement, a vector of response scores RSV. The response score relates to the capability of determining cognitive load 20: The higher a response score for a predicted verbal response 32 is, the more promising the predicted verbal response is for determining cognitive load. Hence, the response scores can be used to pick the (generated) verbal statement best suited for the determination of cognitive load 20.

Generating 110 the at least one verbal statement 30 capable of provoking the at least one verbal response 31 from the user may further comprise e.g. discarding one or more predicted verbal responses 32, if the corresponding one or more response scores do not satisfy a threshold condition (e.g. if a response score is too low). In case of discard, the list of predicted verbal responses, the vector of response probabilities RPV, and/or the vector of response scores RSV need to be adjusted/updated accordingly.

Generating 110 the at least one verbal statement 30 capable of provoking the at least one verbal response 31 from the user may further comprise applying a verbal response selection algorithm configured to select one of the one or more candidate verbal statements based on the one or more vectors of response probabilities RPV and on the one or more vectors of response scores RSV, thereby generating the at least one verbal statement 30 based on the at least one predicted verbal response 32 suitable for determining the cognitive load 20 of the user.

The one or more candidate verbal statements, the one or more predicted verbal responses 32 for each candidate verbal statement, the corresponding one or more response probabilities, and/or the corresponding one or more response scores can be stored in a response database 220. In so doing, such data can later be used to improve the algorithms, in particular the machine learning algorithms. In the latter case, such data may be added or incorporated into a larger training data set machine learning algorithms are trained on. In so doing, the creative work system 200 can be continuously improved, especially in case of internet connectivity ("internet of things").

Assigning a response score to a predicted verbal response may comprise simulatively assessing cognitive load of predicted verbal responses 32. To this end, each predicted verbal response 32 can be synthesized to an audio signal (that does not necessarily is played on the audio interface) to be analyzed in terms of cognitive load. Alternatively, or in addition, each predicted verbal response 32 is analyzed in terms of its semantics (i.e. without synthesizing an audio signal).

Assigning a response score to each predicted verbal response 32 may comprise checking for one or more verbal features in each predicted verbal response and computing a feature score for each of the one or more verbal features. A (i.e. any) verbal feature may comprise or be a verbal feature of a first type comprising a variety of phoneme use, a variety of pseudo-syllable use, or a response length.

A pseudo-syllable is known to be a syllable-like pattern made up of multiple phonemes. Examples of pseudo-syllables may be demonstrated in the voiced sentence "the dog" which can be split into two standard syllables ("the" and "dog") but could also be split into multiple combinations of voiced (non-standard) pseudo-syllables using the same phonemes such as ("thed" and "og") or ("th", "ud", and "og"). In general, what pseudo-syllables are may depend on the accent of the speaker or a speaker's particular emphasis of different vowels and consonants. Like a normal syllable pseudo-syllables may be constructed by the voiced phonemes corresponding to at least one vowel as well as usually voiced sounds of the consonants on at least one side of the at least one vowel (or on either side thereof). However, they are referred to as pseudo-syllables as they may not correspond to an accepted syllable structure of the given language of interest. In fact, typically, a syllable is considered to have a structure consisting of onset, nucleus, and coda. A pseudo-syllable may have part of this structure but miss other parts or may be composed of non-standard combinations of voiced consonants and vowels. In applications where only assessment of the audio qualities of speech audio is required speech may be segmented into pseudo-syllables, regardless of whether or not they constitute syllables according to the standard structure.

Furthermore, a (i.e. any) verbal feature may comprise or be a verbal feature of a second type comprising a second type class for a linguistic object in a sentence, at least one noun, at least one adjective, or at least one phrase, capable of identifying the at least one contemporaneous feature 40 of the creative work 10.

Checking for one or more verbal features in each predicted verbal response 32 and computing the feature score for each of the one or more verbal features may comprise applying each predicted verbal response 32 to a phoneme use algorithm configured to identify at least one phoneme of the predicted verbal response based on a predetermined list of phonemes, and to count the phonemes of the predicted verbal response, and to count unique phonemes of the predicted verbal response, and to divide the count of unique phonemes of the predicted verbal response by the count of the phonemes of the predicted verbal response, thereby computing the verbal feature score, e.g. a phoneme score. As an example, if every phoneme in the text is the same, the score would be close to 0. If every phoneme in the text is different, the score would be 1.

Furthermore, checking for one or more verbal features in each predicted verbal response 32 and computing the feature score for each of the one or more verbal features may comprise applying each predicted verbal response to a pseudo-syllable use algorithm configured to identify at least one pseudo-syllable of the predicted verbal response based on a set of at least one predetermined rule (e.g. any string of characters consisting of one or more vowels and a consonant), and to count the pseudo-syllables of the predicted verbal response, and to count the unique pseudo-syllables of the predicted verbal response, and to divide the count of unique pseudo-syllables by the count of the unique pseudo-syllables, thereby computing the verbal feature score, e.g. a pseudo-syllable score.

Furthermore, checking for one or more verbal features in each predicted verbal response 32 and computing the feature score for each of the one or more verbal features may comprise applying each predicted verbal response to a response length algorithm configured to identify at least one word of the predicted verbal response, and to count the words, and to compute the verbal feature score, e.g. a response length score, based on a comparison of the count of the words to a predetermined reference value. An ideal predetermined reference value can be a response length that is long enough that any increase in length would not appreciably add value in terms of instances of new vocal features. As an example, a sentence with 15 words may have far more utility than a sentence with just two words. On the other hand, a sentence with 100 words may only be marginally more useful than one with 50 words. Realistically, this length would have to be determined experimentally, and may also include adjustments for considerations based on user-friendliness (e.g. a 30 word response may be ideal, but if only a fraction of users actually respond with this many words it would not be a useful reference value).

Furthermore, checking for one or more verbal features in each predicted verbal response 32 and computing the feature score for each of the one or more verbal features may comprise applying each predicted verbal response to a language algorithm configured to identify the verbal features of a second type class of the predicted verbal response, and to count words of the verbal features of the second type class of the predicted verbal response, and to count words of the predicted verbal response, and to divide the count of words of the verbal features of the second type class of the predicted verbal response by the count of the words of the predicted verbal response, thereby computing the verbal feature score.

Assigning a response score to each predicted verbal response 32 may be based on at least one verbal feature score corresponding to at least one verbal feature of the predicted verbal response. The response score to each predicted verbal response 32 can be computed as an average of the verbal feature scores corresponding to the one or more verbal features of the predicted verbal response.

Selecting one of the one or more candidate verbal statements based on the one or more vectors of response probabilities RPV and on the one or more vectors of response scores RSV may comprise multiplying (i.e. component-wise), for each candidate verbal statement, the vector of response probabilities RPV and the vector of response scores RSV, thereby generating, for each candidate verbal statement, a vector of weighted response scores $$WRSV = RPV.*RSV$$

and summing, for each candidate verbal statement, components of the vector of weighted response scores WRSV, thereby generating, for each candidate verbal statement, a total selection score, and selecting one of the one or more candidate verbal statements with the highest total selection score.

Obtaining 130 the at least one verbal response 31 from the user via the audio interface 211 may comprise obtaining the at least one verbal response from the user in terms of a timestamped audio waveform (e.g. in terms of an audio waveform and a timestamp marking a starting point of the audio waveform).

Determining 140 the cognitive load 20 of the user based on the at least one verbal response 31 obtained from the user may comprise assessing at least one vocal feature of the at least one verbal response obtained from the user. A vocal feature may be a verbal feature of the first type or a change in pitch with respect to time, or a periodicity or a variation in low-frequency glottal pulses.

Determining 140 the cognitive load 20 of the user based on the at least one verbal response 31 obtained from the user may comprise applying one or more cognitive load feature assessment algorithms (along the lines of Quatieri et al.), wherein each cognitive load feature assessment algorithm corresponds to a vocal feature and is configured to generate a vocal feature vector representation of the corresponding vocal feature for the at least one verbal response 31 from the user, thereby generating one or more vocal feature vector representations.

Determining 140 the cognitive load 20 of the user based on the at least one verbal response 31 obtained from the user may comprises applying the one or more vocal feature vector representations to a cognitive load score algorithm configured to compare each of the one or more vocal feature vector representations to at least one predetermined benchmark for cognitive load, wherein each comparison comprises computing a predetermined criterion (e.g. each vocal feature vector representation may have a predetermined criterion of its own.) based on at least one vocal feature vector representation and the at least one predetermined benchmark for cognitive load, and to count the one or more vocal feature vector representations satisfying the corresponding predetermined criteria, and to count the one or more vocal feature vector representations, and to divide a count of the one or more vocal feature vector representations satisfying the corresponding predetermined criteria by a count of the one or more vocal feature vector representations, thereby determining the cognitive load score of the user, thereby determining the cognitive load 20 of the user. The cognitive load score may e.g. be a real number in the interval [0, 1] (including the boundaries). Note that vocal features may have different predetermined benchmarks for cognitive load. The predetermined benchmark for cognitive load may vary depending on the vector representation of the vocal feature. A simple case would be a set of "benchmark" vectors, one for each feature type, which can be used for direct element-by-element comparison with the measured feature vectors. Furthermore, as an example, it is possible to compare an eigenvalue spectrum of a set of "high cognitive load" feature vectors to an eigenvalue spectrum of "low cognitive load" feature vectors. In that case, the benchmark may be an eigenvalue spectrum which represents the threshold between low and high cognitive load.

The cognitive load score may inherit a timestamp of the timestamped audio waveform. The cognitive load score and the corresponding timestamp may be stored in a score database 220, 221.

Generating 151 the at least one further verbal statement 50 capable of provoking at least one further verbal response 51 from the user may comprise selecting a question about the at least one contemporaneous feature 40. Some generated verbal statements may have been tagged initially as "question statements". They can be questions which will encourage the user to respond with a response that contains information on the contemporaneous feature 40 of the creative work. They need not be specific to any particular feature but can be general questions, along the lines of e.g. "what are you drawing now?" or "what are you working on now?", see FIG. 4b. The audio interface may vocalize these question statements each time it determines the cognitive load of a user, and the user gives some response which is analyzed. Therefore, it can be said that the user response used for determining cognitive load is contemporaneous to the user response used for determining the created feature, i.e. the determined cognitive load is related to that created feature, i.e. the contemporaneous feature 40. Because the receipt of each user response can be timestamped, these timestamps can be used to identify the contemporaneous cognitive loads and the created (contemporaneous) features.

Obtaining 154 the at least one further verbal response 51 from the user via the audio interface 211 may comprise obtaining the at least one further verbal response from the user in terms of a further timestamped audio waveform (e.g. in terms of a further audio waveform and a further timestamp marking a starting point of the further audio waveform).

The at least one further verbal response 51 from the user can be applied to a speech-to-text algorithm, thereby generating a verbal feature string inheriting a further timestamp from the further timestamped audio waveform. The generated verbal feature string may be used for the record or report after completion of the creative work 10, cf. FIG. 5c. Alternatively, or in addition, the at least one verbal response 31 from the user is applied to a speech-to-text algorithm, thereby generating a verbal feature string inheriting a further timestamp from the timestamped audio waveform.

Determining 155 the at least one contemporaneous feature 40 of the creative work 10 based on the obtained at least one verbal response 31 from the user or on the obtained at least one further verbal response 51 from the user may comprise applying the verbal feature string to a feature recognition algorithm configured to identify a noun that most likely relates to the at least one contemporaneous feature of the creative work.

Identifying the at least one contemporaneous feature 40 of the creative work 10 may comprise applying a text split algorithm configured to break the verbal feature string into one or more subunits each comprising sentences, phrases, clauses, and/or words, and applying a noun extraction algorithm configured to perform a look-up for one or more subunits in a generic dictionary providing the at least one noun for the at least one contemporaneous feature of the creative work, and e.g., applying a noun selection algorithm configured to select a noun that most likely relates to the at least one contemporaneous feature 40 of the creative work 10 based on one or more provided nouns, thereby identifying the noun that most likely relates to the at least one contemporaneous feature of the creative work. As an example, see FIG. 4*b*, "apple" may be extracted and recognized from "I am drawing a big red apple.".

The feature recognition algorithm, e.g. the text split algorithm, the noun extraction algorithm and/or the noun selection algorithm, may comprise at least one pre-trained machine learning algorithm, e.g. providing more than one answers with corresponding probabilities.

The noun that most likely relates to the at least one contemporaneous feature 40 of the creative work 10 may inherit the further timestamp of the verbal feature string. The at least one contemporaneous feature 40 of the creative work 10, the noun that most likely relates to the at least one contemporaneous feature of the creative work and the further timestamp, and e.g. the verbal feature string may be stored in the score database 220, 221.

In an embodiment, the method 100 may further comprise generating 160 at least one tailored response 60 based on the cognitive load 20 and/or the corresponding contemporaneous feature 40, wherein, as an example, the at least one tailored response aims at influencing the user of the creative work system 200, see FIG. 5*a-c*. The at least one tailored response 60 may comprise psychological means to engage the user with the creative work 10. Such psychological means may comprise encouragement and/or praise. Furthermore, generating 160 the at least one tailored response 60 may be triggered by a request of a user or of a further individual (e.g. a supervisor or teacher), or automatically when the cognitive load 20 exceeds a predetermined cognitive load threshold. Furthermore In an embodiment, the method 100 may further comprising generating 161 at least one further tailored response 60 based on at least one cognitive load 20 and/or the at least one corresponding contemporaneous feature 40 queried from the score database 220, 221. In other words, the at least one further tailored response 60 may refer to one or more contemporaneous features of the past. This can be used to generate and output a record or a report e.g. after completion of the creative work and covering a period of time in the past. Querying at least one cognitive load 20 and/or the at least one corresponding contemporaneous feature 40 can be subject to one or more conditions comprising a condition restricting stored timestamps, and a condition restricting stored cognitive loads, and a condition restricting stored contemporaneous features. Such conditions may be set via the user interface 210. As an example, a condition can be "all cognitive load (scores) above a threshold and within the past five minutes".

The at least one tailored response 60 can be based on a tailored response template 61, see e.g. FIG. 5*a-c*, e.g. queried from a tailored response template database 220. Other parameters such as e.g. a name of the user may be used in this retrieval as well. The tailored response template 61 may be a parametrizable text. Furthermore, generating 160, 161 the at least one tailored response 60 based on the cognitive load 20 and the corresponding contemporaneous feature 40 may comprise applying a tailored response algorithm configured to integrate at least one cognitive load, the at least one corresponding contemporaneous feature, and/or at least one corresponding timestamp into the tailored response template 61. A verbal statement, and/or e.g. a tailored response may comprise a name of the user.

The method 100 may comprise outputting 170 the at least one tailored response via a user interface 210 to the user, e.g. on a graphical interface 214 and/or via the audio interface 211.

The at least one generated tailored response 60 can be capable of provoking a third response (e.g. "yes" or "no") 62 from the user, and the method further may comprise prompting the user to vocally interact with the creative work system 200 by vocalizing the at least one generated tailored response 60, and obtaining the third response 62 from the user via the user interface 210 (e.g. a button of the user interface 210 or the audio interface 211), e.g. the audio interface 211, and executing a third response algorithm based on the third response 62 from the user, e.g. wherein the third response algorithm is configured to feed back 180 information related to the at least one cognitive load 20 and/or the at least one corresponding contemporaneous feature 40 via the user interface 210, if the third response 62 from the user is recognized to be affirmative. In other words, feeding back 180 such information may be carried out if the third response algorithm recognizes a "yes" in the third response 62 from the user. The information related to the at least one cognitive load 20 and/or the at least one corresponding contemporaneous feature 40 may contribute to creating the creative work 10. As an example, the information may comprise an image or a video tutorial on how to draw an object (e.g. an apple), see FIG. 5*c*, display on the graphical interface 214.

Figure 1A:
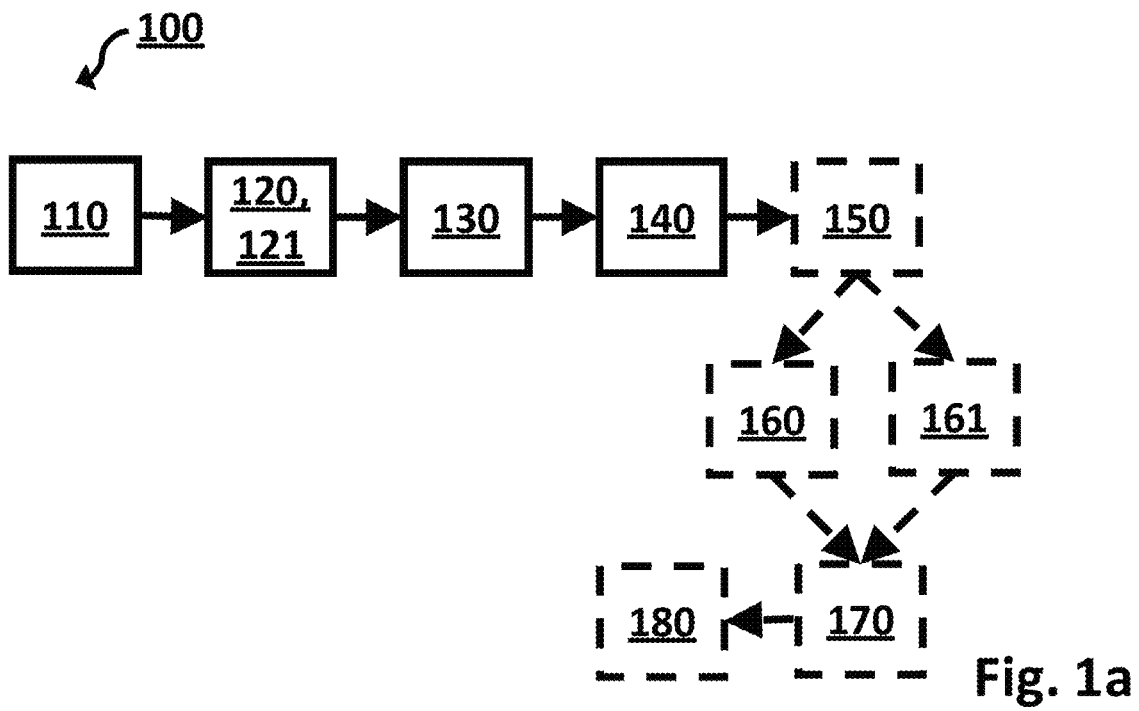
Figure 1B:
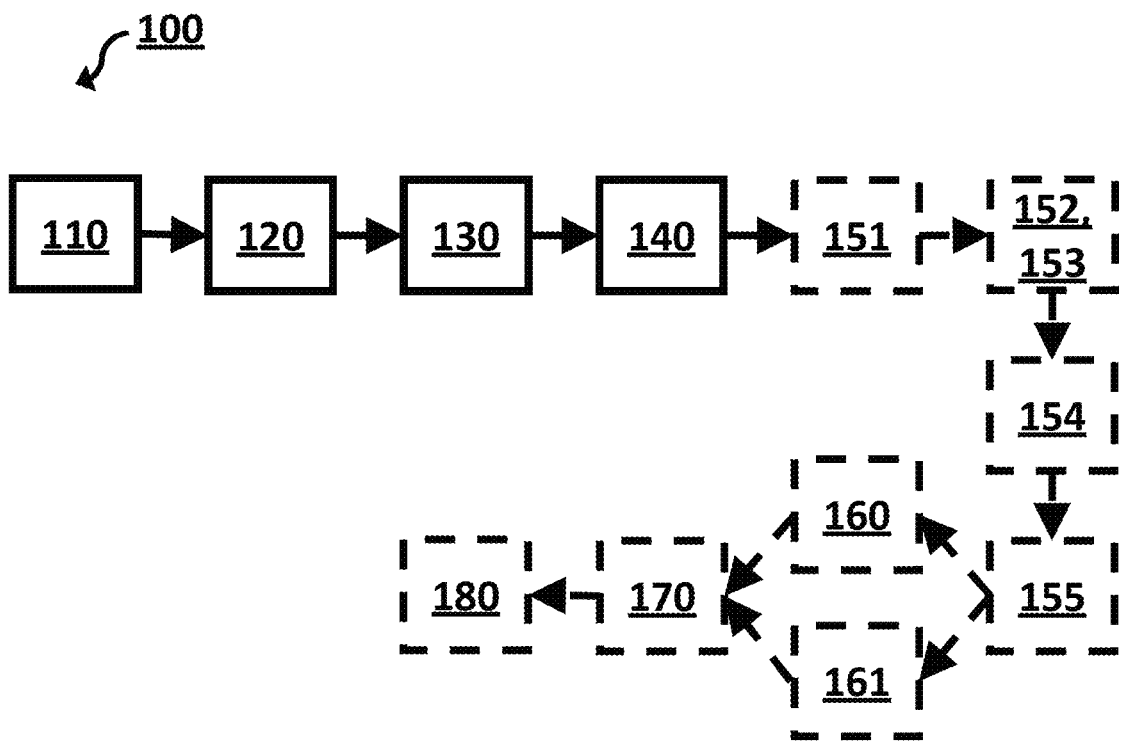
Figure 2A:
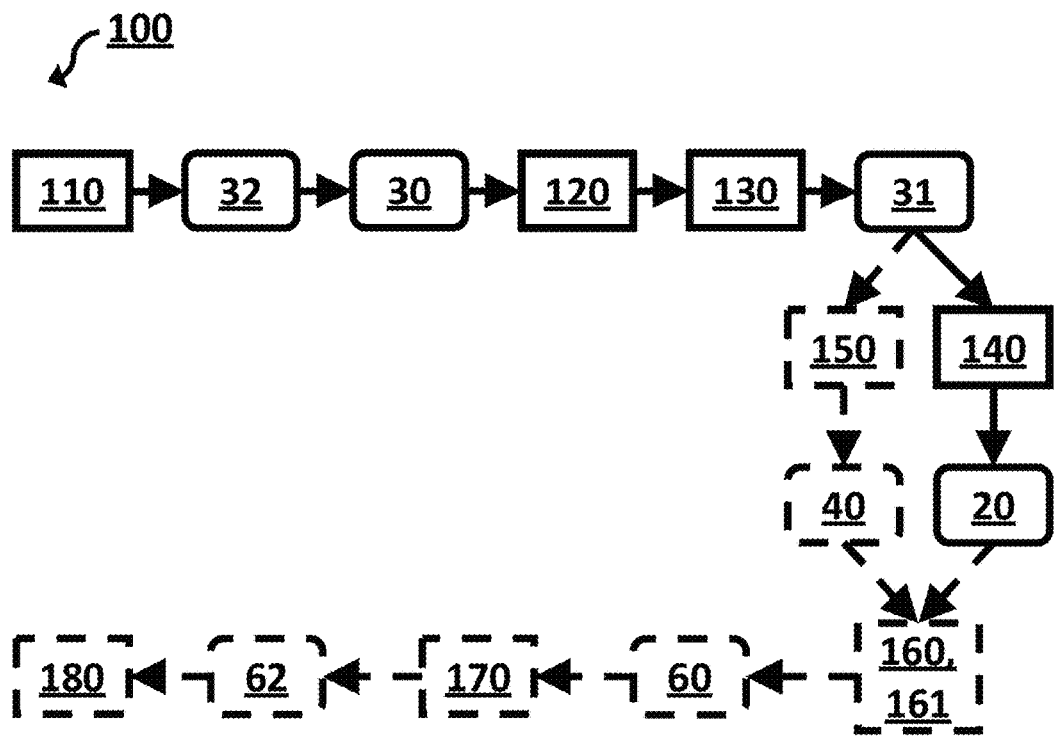
Figure 2B:
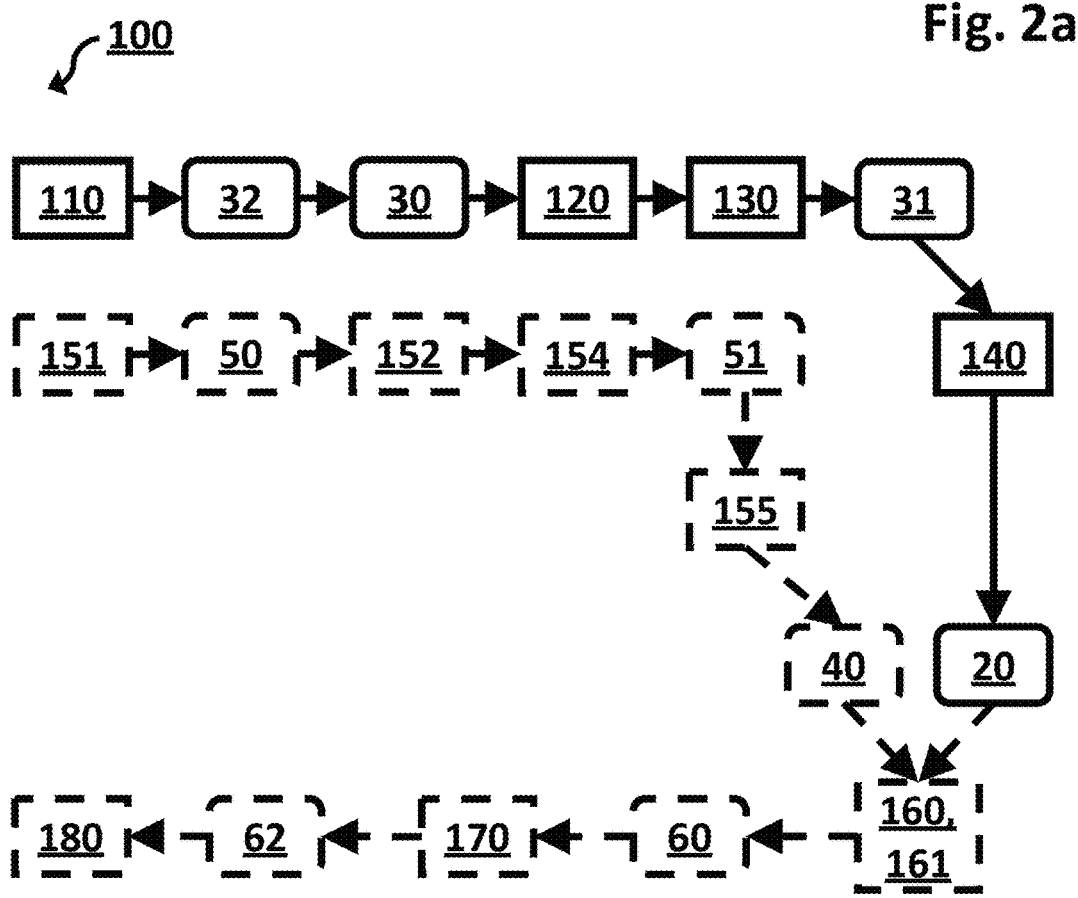

FIG. 2*a-b* schematically illustrate embodiments of the computer-implemented method 100 according to the first aspect for measuring cognitive load 20 of the user creating the creative work 10 in a creative work system 200. In FIG. 2*a*, both the cognitive load 20 of the user and the contemporaneous feature 40 are determined based on the verbal response 31 from the user. On the other hand, in FIG. 2*b*, the cognitive load 20 of the user is determined based on the verbal response 31 from the user and the contemporaneous feature 40 is determined based on the further verbal response 51 from the user.

Figure 3:
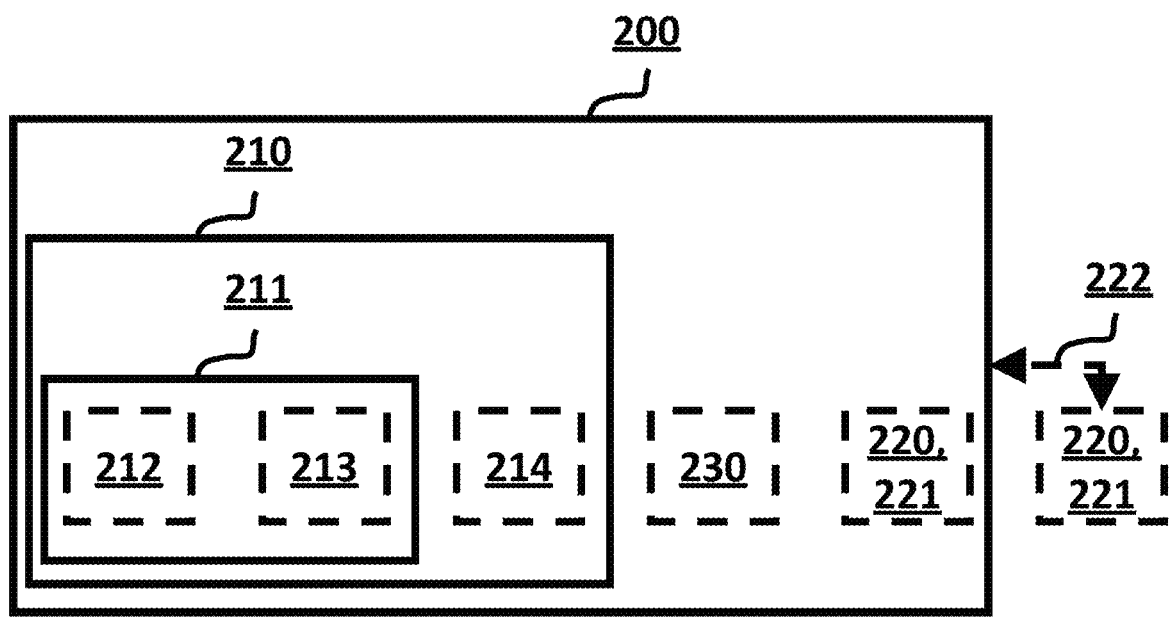

The creative work system 200 for measuring cognitive load 20 of a user creating the creative work 10 may comprise a user interface 210 comprising an audio interface 211. The creative work system may be configured to run the method 100 of the first aspect (or an embodiment thereof). FIG. 3 schematically illustrates the creative work system 200.

The audio interface 211 may comprise at least one microphone 212 and at least one speaker 213 (i.e. a loudspeaker).

The creative work system 200 may comprise access to at least one database 220, e.g. to the score database 221, via a communication channel 222. A database 220, or the score database 221, may either be part of the creative work system 200 or accessed via a communication channel 222.

The creative work system 200 may comprise a camera 230 configured to record at least one image or a sequence of images of the creative work 10 as creation progresses. This can be used to determine cognitive load also by analyzing a captured video sequence (e.g. based on eye tracking) of the user. In so doing, the accuracy of the determination of the (overall) cognitive load can be improved (e.g. by averaging over auditive and visual cognitive load scores). Alternatively, or in addition, a visual object-recognition algorithm (e.g. a pre-trained image recognition model) may be applied that is configured to identify one or more visual features of the creative work 10 and to correlate them to cognitive load (e.g. via timestamp matching).

The user interface 210 may comprise a graphical interface 214. This can be used to display information such as images or videos.

Figure 6:
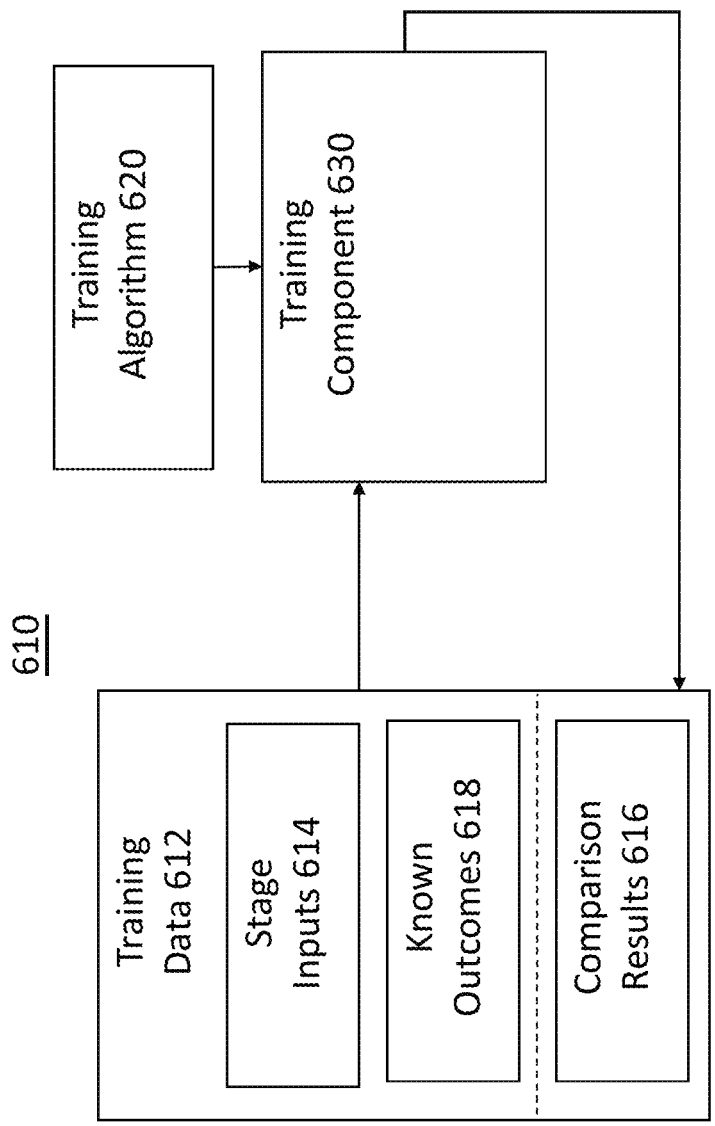
FIG. 6 shows an example machine learning training flow chart.

One or more implementations disclosed herein include and/or may be implemented using a machine learning model. For example, one or more of the response algorithm, candidate verbal statement algorithm, conversation algorithm, common predictive communication algorithm, predicted verbal response assessment algorithm, verbal response selection algorithm, machine learning algorithms, phoneme use algorithm, pseudo-syllable use algorithm, response length algorithm, language algorithm, cognitive load feature assessment algorithm, cognitive load score algorithm, speech-to-text algorithm, feature recognition algorithm, text split algorithm, noun extraction algorithm, noun selection algorithm, pre-trained machine learning algorithm and/or visual object-recognition algorithm may be implemented using a machine learning model and/or may be used to train a machine learning model. A given machine learning model may be trained using the data flow 610 of FIG. 6. Training data 612 may include one or more of stage inputs 614 and known outcomes 618 related to a machine learning model to be trained. The stage inputs 614 may be from any applicable source including text, visual representations, data, values, comparisons, stage outputs (e.g., one or more outputs from a step from FIGS. 1a, 1b, 2a, 2b, and/or 3). The known outcomes 618 may be included for machine learning models generated based on supervised or semi-supervised training. An unsupervised machine learning model may not be trained using known outcomes 618. Known outcomes 618 may include known or desired outputs for future inputs similar to or in the same category as stage inputs 614 that do not have corresponding known outputs.

The training data 612 and a training algorithm 620 (e.g., response algorithm, candidate verbal statement algorithm, conversation algorithm, common predictive communication algorithm, predicted verbal response assessment algorithm, verbal response selection algorithm, machine learning algorithms, phoneme use algorithm, pseudo-syllable use algorithm, response length algorithm, language algorithm, cognitive load feature assessment algorithm, cognitive load score algorithm, speech-to-text algorithm, feature recognition algorithm, text split algorithm, noun extraction algorithm, noun selection algorithm, pre-trained machine learning algorithm and/or visual object-recognition algorithm implemented using a machine learning model and/or may be used to train a machine learning model) may be provided to a training component 630 that may apply the training data 612 to the training algorithm 620 to generate a machine learning model. According to an implementation, the training component 630 may be provided comparison results 616 that compare a previous output of the corresponding machine learning model to apply the previous result to re-train the machine learning model. The comparison results 616 may be used by the training component 630 to update the corresponding machine learning model. The training algorithm 620 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, and/or discriminative models such as Decision Forests and maximum margin methods, or the like.

A machine learning model used herein may be trained and/or used by adjusting one or more weights and/or one or more layers of the machine learning model. For example, during training, a given weight may be adjusted (e.g., increased, decreased, removed) based on training data or input data. Similarly, a layer may be updated, added, or removed based on training data/and or input data. The resulting outputs may be adjusted based on the adjusted weights and/or layers.

In general, any process or operation discussed in this disclosure that is understood to be computer-implementable, such as the process illustrated in FIGS. 1a, 1b, 2a, 2b, and/or 3 may be performed by one or more processors of a computer system as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices. One or more processors of a computer system may be included in a single computing device or distributed among a plurality of computing devices. One or more processors of a computer system may be connected to a data storage device. A memory of the computer system may include the respective memory of each computing device of the plurality of computing devices.

Figure 7:
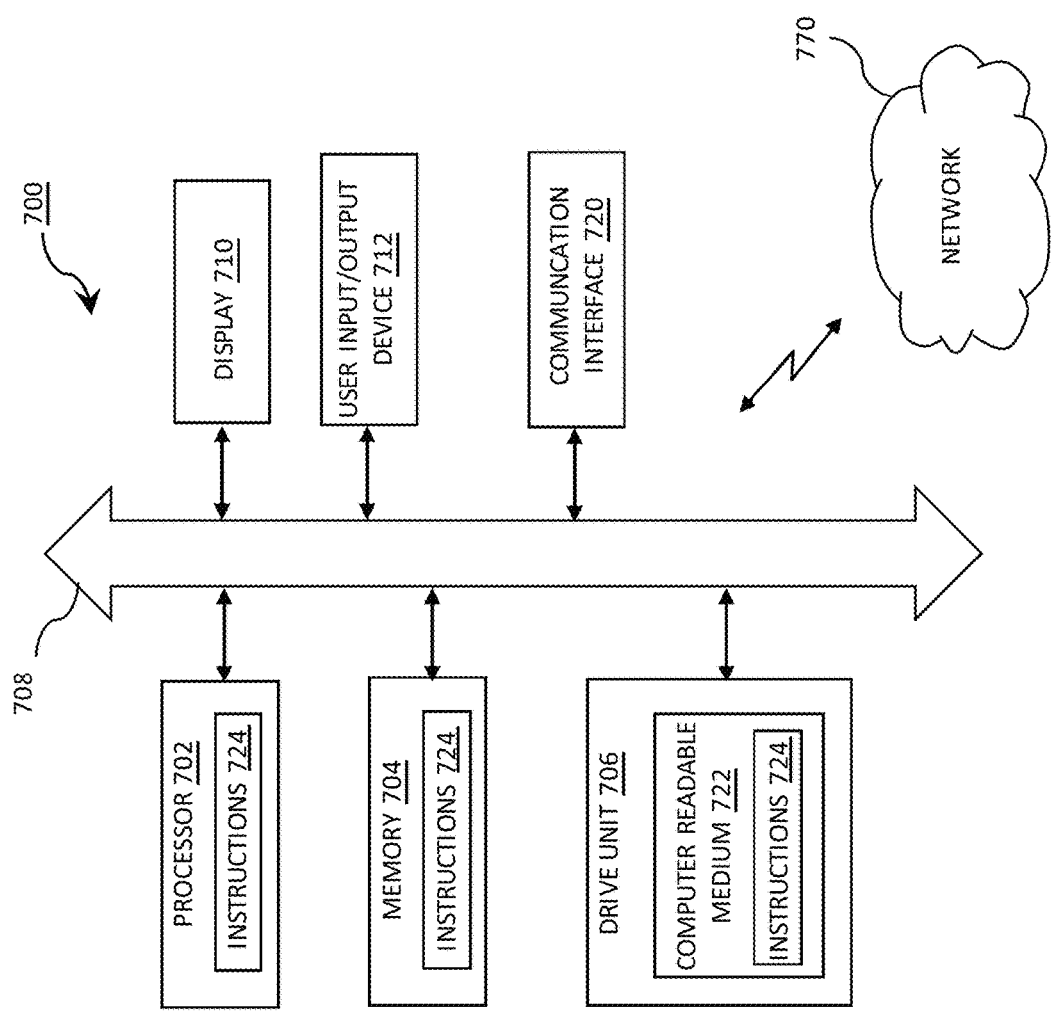
FIG. 7 illustrates an implementation of a general computer system that may execute techniques presented herein.

In various embodiments, one or more portions of method 100 and system 200 may be implemented in, for instance, a chip set including a processor and a memory as shown in FIG. 7. FIG. 7 illustrates an implementation of a general computer system that may execute techniques presented herein. The computer system 700 can include a set of instructions that can be executed to cause the computer system 700 to perform any one or more of the methods or computer based functions disclosed herein. The computer system 700 may operate as a standalone device or may be connected, e.g., using a network, to other computer systems or peripheral devices.

Unless specifically stated otherwise, as apparent from the following discussions, it is appreciated that throughout the specification, discussions utilizing terms such as "processing," "computing," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer," a "computing machine," a "computing platform," a "computing device," or a "server" may include one or more processors.

In a networked deployment, the computer system 700 may operate in the capacity of a server or as a client user computer in a server-client user network environment, or as a peer computer system in a peer-to-peer (or distributed) network environment. The computer system 700 can also be implemented as or incorporated into various devices, such as a personal computer (PC), a tablet PC, a personal digital assistant (PDA), a mobile device, a palmtop computer, a laptop computer, a desktop computer, a communications device, a wireless telephone, a land-line telephone, a control system, a camera, a scanner, a facsimile machine, a personal trusted device, a web appliance, a network router, switch or bridge, or any other machine capable of executing a set of instructions (sequential or otherwise) that specify actions to be taken by that machine. In a particular implementation, the computer system 700 can be implemented using electronic devices that provide voice, video, or data communication. Further, while a computer system 700 is illustrated as a single system, the term "system" shall also be taken to include any collection of systems or sub-systems that individually or jointly execute a set, or multiple sets, of instructions to perform one or more computer functions.

As illustrated in FIG. 7, the computer system 700 may include a processor 702, e.g., a central processing unit (CPU), a graphics processing unit (GPU), or both. The processor 702 may be a component in a variety of systems. For example, the processor 702 may be part of a standard personal computer or a workstation. The processor 702 may be one or more general processors, digital signal processors, application specific integrated circuits, field programmable gate arrays, servers, networks, digital circuits, analog circuits, combinations thereof, or other now known or later developed devices for analyzing and processing data. The processor 702 may implement a software program, such as code generated manually (i.e., programmed).

The computer system 700 may include a memory 704 that can communicate via a bus 708. The memory 704 may be a main memory, a static memory, or a dynamic memory. The memory 704 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 704 includes a cache or random-access memory for the processor 702. In alternative implementations, the memory 704 is separate from the processor 702, such as a cache memory of a processor, the system memory, or other memory. The memory 704 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 704 is operable to store instructions executable by the processor 702. The functions, acts or tasks illustrated in the figures or described herein may be performed by the processor 702 executing the instructions stored in the memory 704. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 700 may further include a display 710, such as a liquid crystal display (LCD), an organic light emitting diode (OLED), a flat panel display, a solid-state display, a cathode ray tube (CRT), a projector, a printer or other now known or later developed display device for outputting determined information. The display 710 may act as an interface for the user to see the functioning of the processor 702, or specifically as an interface with the software stored in the memory 704 or in the drive unit 706.

Additionally or alternatively, the computer system 700 may include an input/output device 712 configured to allow a user to interact with any of the components of computer system 700. The input/output device 712 may be a number pad, a keyboard, or a cursor control device, such as a mouse, or a joystick, touch screen display, remote control, or any other device operative to interact with the computer system 700.

The computer system 700 may also or alternatively include drive unit 706 implemented as a disk or optical drive. The drive unit 706 may include a computer-readable medium 722 in which one or more sets of instructions 724, e.g. software, can be embedded. Further, instructions 724 may embody one or more of the methods or logic as described herein. The instructions 724 may reside completely or partially within the memory 704 and/or within the processor 702 during execution by the computer system 700. The memory 704 and the processor 702 also may include computer-readable media as discussed above.

In some systems, a computer-readable medium 722 includes instructions 724 or receives and executes instructions 724 responsive to a propagated signal so that a device connected to a network 770 can communicate voice, video, audio, images, or any other data over the network 770. Further, the instructions 724 may be transmitted or received over the network 770 via a communication port or interface 720, and/or using a bus 708. The communication port or interface 720 may be a part of the processor 702 or may be a separate component. The communication port or interface 720 may be created in software or may be a physical connection in hardware. The communication port or interface 720 may be configured to connect with a network 770, external media, the display 710, or any other components in computer system 700, or combinations thereof. The connection with the network 770 may be a physical connection, such as a wired Ethernet connection or may be established wirelessly as discussed below. Likewise, the additional connections with other components of the computer system 700 may be physical connections or may be established wirelessly. The network 770 may alternatively be directly connected to a bus 708.

While the computer-readable medium 722 is shown to be a single medium, the term "computer-readable medium" may include a single medium or multiple media, such as a centralized or distributed database, and/or associated caches and servers that store one or more sets of instructions. The term "computer-readable medium" may also include any medium that is capable of storing, encoding, or carrying a set of instructions for execution by a processor or that cause a computer system to perform any one or more of the methods or operations disclosed herein. The computer-readable medium 722 may be non-transitory, and may be tangible.

The computer-readable medium 722 can include a solid-state memory such as a memory card or other package that houses one or more non-volatile read-only memories. The computer-readable medium 722 can be a random-access memory or other volatile re-writable memory. Additionally or alternatively, the computer-readable medium 722 can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative implementation, dedicated hardware implementations, such as application specific integrated circuits, programmable logic arrays and other hardware devices, can be constructed to implement one or more of the methods described herein. Applications that may include the apparatus and systems of various implementations can broadly include a variety of electronic and computer systems. One or more implementations described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The computer system 700 may be connected to a network 770. The network 770 may define one or more networks including wired or wireless networks. The wireless network may be a cellular telephone network, an 802.11, 802.16, 802.20, or WiMAX network. Further, such networks may include a public network, such as the Internet, a private network, such as an intranet, or combinations thereof, and may utilize a variety of networking protocols now available or later developed including, but not limited to TCP/IP based networking protocols. The network 770 may include wide area networks (WAN), such as the Internet, local area networks (LAN), campus area networks, metropolitan area networks, a direct connection such as through a Universal Serial Bus (USB) port, or any other networks that may allow for data communication. The network 770 may be configured to couple one computing device to another computing device to enable communication of data between the devices. The network 770 may generally be enabled to employ any form of machine-readable media for communicating information from one device to another. The network 770 may include communication methods by which information may travel between computing devices. The network 770 may be divided into sub-networks. The sub-networks may allow access to all of the other components connected thereto or the sub-networks may restrict access between the components. The network 770 may be regarded as a public or private network connection and may include, for example, a virtual private network or an encryption or other security mechanism employed over the public Internet, or the like.

In accordance with various implementations of the present disclosure, the methods described herein may be implemented by software programs executable by a computer system. Further, in an exemplary, non-limited implementation, implementations can include distributed processing, component/object distributed processing, and parallel processing. Alternatively, virtual computer system processing can be constructed to implement one or more of the methods or functionality as described herein.

Although the present invention has been described above and is defined in the attached claims, it should be understood that the invention may alternatively be defined in accordance with the following embodiments:

1. A computer-implemented method (100) for measuring cognitive load (20) of a user creating a creative work (10) in a creative work system (200), comprising:
    generating (110) at least one verbal statement (30) capable of provoking at least one verbal response (31) from the user; and
    prompting (120) the user to vocally interact with the creative work system by vocalizing (121) the at least one generated verbal statement (30) to the user via an audio interface (211) of the creative work system; and
    obtaining (130) the at least one verbal response (31) from the user via the audio interface; and
    determining (140) the cognitive load (20) of the user based on the at least one verbal response (31) obtained from the user;
    wherein generating (110) the at least one verbal statement (30) is based on at least one predicted verbal response (32) suitable for determining the cognitive load (20) of the user.

2. The method (100) of embodiment 1, further comprising:
    determining (150) at least one contemporaneous feature (40) of the creative work (10) based on the at least one obtained verbal response (31) from the user.

3. The method (100) of embodiment 1, further comprising:
    generating (151) at least one further verbal statement (50) capable of provoking at least one further verbal response (51) from the user; and
    prompting (152) the user to vocally interact with the creative work system (200) by vocalizing (153) the at least one generated further verbal statement (50) to the user via an audio interface (211) of the creative work system; and
    obtaining (154) at least one further verbal response (51) from the user via the audio interface; and
    determining (155) at least one contemporaneous feature (40) of the creative work (10) based on the at least one obtained further verbal response (51) from the user.

4. The method (100) of one of the preceding embodiments, wherein the creative work (10) comprises a visual artwork.

5. The method (100) of embodiment 4, wherein the visual artwork comprises a drawing, a painting, calligraphy and/or a sculpture.

6. The method (100) of one of the preceding embodiments, wherein the creative work (10) comprises writing.

7. The method (100) of one of the preceding embodiments, wherein the at least one verbal response (31) from the user is spoken language.

8. The method (100) of one of the preceding embodiments, when dependent on embodiment 3, wherein the at least one further verbal response (51) from the user is spoken language.

9. The method (100) of one of the preceding embodiments, wherein the audio interface (211) of the creative work system (200) comprises at least one microphone (212) and at least one speaker (213).

10. The method (100) of one of the preceding embodiments, wherein vocalizing (121) the at least one generated verbal statement (30) to the user via the audio interface (211) of the creative work system (200) comprises:
   synthesizing at least one audio signal representing the at least one generated verbal statement; and
   playing the at least one audio signal on the audio interface of the creative work system.
11. The method (100) of one of the preceding embodiments, when dependent on embodiment 3, wherein vocalizing (153) the at least one further generated verbal statement (50) to the user via the audio interface (211) of the creative work system (200) comprises:
   synthesizing at least one further audio signal representing the at least one further generated verbal statement; and
   playing the at least one further audio signal on the audio interface of the creative work system.
12. The method (100) of one of the preceding embodiments, when dependent on embodiment 2 or 3, wherein the at least one contemporaneous feature (40) of the creative work (10) comprises at least one feature of the creative work the user of the creative work system (200):
   has just completed; or
   is currently working on; or
   is going to work on next.
13. The method (100) of embodiment 12, wherein the at least one feature of the creative work (10) comprises one or more of:
   a part of the creative work; and
   an object featured by the creative work; and
   an aspect of the creative work the user of the creative work can vocally refer to, name, describe, and/or specify.
14. The method (100) of one of the preceding embodiments, wherein generating (110) the at least one verbal statement (30) capable of provoking the at least one verbal response (31) from the user comprises:
   applying a candidate verbal statement algorithm configured to generate one or more candidate verbal statements; and
   applying a conversation algorithm configured to generate for each candidate verbal statement one or more predicted verbal responses (32) and corresponding one or more response probabilities, thereby generating, for each candidate verbal statement, a list of predicted verbal responses and a vector of response probabilities RPV; and
   applying a predicted verbal response assessment algorithm configured to assign a response score to each predicted verbal response (32), thereby generating, for each candidate verbal statement, a vector of response scores; and applying a verbal response selection algorithm configured to select one of the one or more candidate verbal statements based on the one or more vectors of response probabilities and on the one or more vectors of response scores, thereby generating the at least one verbal statement (30) based on the at least one predicted verbal response (32) suitable for determining the cognitive load (20) of the user.
15. The method (100) of embodiment 14, wherein the one or more candidate verbal statements, the one or more predicted verbal responses (32) for each candidate verbal statement, the corresponding one or more response probabilities, and/or the corresponding one or more response scores are stored in a response database (220).
16. The method (100) of embodiment 14 or 15, wherein assigning a response score to each predicted verbal response (32) comprises checking for one or more verbal features in each predicted verbal response and computing a feature score for each of the one or more verbal features.
17. The method (100) of embodiment 16, wherein a verbal feature comprises a verbal feature of a first type comprising:
   a variety of phoneme use; or
   a variety of pseudo-syllable use; or
   a response length.
18. The method (100) of embodiment 16 or 17, when dependent on embodiment 2 or 3, wherein a verbal feature comprises a verbal feature of a second type comprising a second type class for:
   a linguistic object in a sentence; or
   at least one noun; or
   at least one adjective; or
   at least one phrase;
   capable of identifying the at least one contemporaneous feature of the creative work (10).
19. The method (100) of one of the embodiments 16 to 18, when dependent on embodiment 17, wherein checking for one or more verbal features in each predicted verbal response (32) and computing the feature score for each of the one or more verbal features comprises applying each predicted verbal response (32) to a phoneme use algorithm configured:
   to identify at least one phoneme of the predicted verbal response based on a predetermined list of phonemes; and
   to count the phonemes of the predicted verbal response; and
   to count unique phonemes of the predicted verbal response; and
   to divide the count of unique phonemes of the predicted verbal response by the count of the phonemes of the predicted verbal response, thereby computing a phoneme score, thereby computing the verbal feature score.
20. The method (100) of one of the embodiments 16 to 19, when dependent on embodiment 17, wherein checking for one or more verbal features in each predicted verbal response (32) and computing the feature score for each of the one or more verbal features comprises applying each predicted verbal response to a pseudo-syllable use algorithm configured:
   to identify at least one pseudo-syllable of the predicted verbal response based on a set of at least one predetermined rule; and
   to count the pseudo-syllables of the predicted verbal response; and
   to count the unique pseudo-syllables of the predicted verbal response; and
   to divide the count of unique pseudo-syllables by the count of the unique pseudo-syllables, thereby computing a pseudo-syllable score, thereby computing the verbal feature score.
21. The method (100) of one of the embodiments 16 to 20, when dependent on embodiment 17, wherein checking for one or more verbal features in each predicted verbal response (32) and computing the feature score for each of the one or more verbal features comprises applying each predicted verbal response to a response length algorithm configured:
- to identify at least one word of the predicted verbal response; and
- to count the words; and
- to compute a response length score, thereby computing the verbal feature score, based on a comparison of the count of the words to a predetermined reference value.

22. The method (100) of one of the embodiments 16 to 21, when dependent on embodiment 18, wherein checking for one or more verbal features in each predicted verbal response (32) and computing the feature score for each of the one or more verbal features comprises applying each predicted verbal response to a language algorithm configured:
- to identify the verbal features of a second type class of the predicted verbal response; and
- to count words of the verbal features of the second type class of the predicted verbal response; and
- to count words of the predicted verbal response; and
- to divide the count of words of the verbal features of the second type class of the predicted verbal response by the count of the words of the predicted verbal response, thereby computing the verbal feature score.

23. The method (100) of one of the embodiments 16 to 22, wherein assigning a response score to each predicted verbal response (32) is based on at least one verbal feature score corresponding to at least one verbal feature of the predicted verbal response.

24. The method (100) of embodiment 23, wherein the response score to each predicted verbal response (32) is computed as an average of the verbal feature scores corresponding to the one or more verbal features of the predicted verbal response.

25. The method (100) of one of the embodiments 14 to 24, wherein selecting one of the one or more candidate verbal statements based on the one or more vectors of response probabilities and on the one or more vectors of response scores comprises:
- multiplying, for each candidate verbal statement, the vector of response probabilities RPV and the vector of response scores, thereby generating, for each candidate verbal statement, a vector of weighted response scores; and
- summing, for each candidate verbal statement, components of the vector of weighted response scores, thereby generating, for each candidate verbal statement, a total selection score; and
- selecting one of the one or more candidate verbal statements with the highest total selection score.

26. The method (100) of one of the preceding embodiments, wherein obtaining (130) the at least one verbal response (31) from the user via the audio interface (211) comprises obtaining the at least one verbal response from the user in terms of a timestamped audio waveform.

27. The method (100) of one of the preceding embodiments, wherein determining (140) the cognitive load (20) of the user based on the at least one verbal response (31) obtained from the user comprises assessing at least one vocal feature of the at least one verbal response obtained from the user.

28. The method (100) of embodiment 27, when dependent on embodiment 17, wherein a vocal feature is a verbal feature of the first type or:
- a change in pitch
- a periodicity or a variation in low-frequency glottal pulses.

29. The method (100) of embodiment 27 or 28, wherein determining (140) the cognitive load (20) of the user based on the at least one verbal response (31) obtained from the user comprises applying one or more cognitive load feature assessment algorithms, wherein each cognitive load feature assessment algorithm corresponds to a vocal feature and is configured:
- to generate a vocal feature vector representation of the corresponding vocal feature for the at least one verbal response (31) from the user,
- thereby generating one or more vocal feature vector representations.

30. The method (100) of embodiment 29, wherein determining (140) the cognitive load (20) of the user based on the at least one verbal response (31) obtained from the user comprises applying the one or more vocal feature vector representations to a cognitive load score algorithm configured:
- to compare each of the one or more vocal feature vector representations to at least one predetermined benchmark for cognitive load, wherein each comparison comprises computing a predetermined criterion based on at least one vocal feature vector representation and the at least one predetermined benchmark for cognitive load; and
- to count the one or more vocal feature vector representations satisfying the corresponding predetermined criteria; and
- to count the one or more vocal feature vector representations; and
- to divide a count of the one or more vocal feature vector representations satisfying the corresponding predetermined criteria by a count of the one or more vocal feature vector representations, thereby determining the cognitive load score of the user, thereby determining the cognitive load (20) of the user.

31. The method (100) of one of the preceding embodiments, when dependent on embodiment 26, wherein the cognitive load score inherits a timestamp of the timestamped audio waveform.

32. The method (100) of embodiment 31, wherein cognitive load score and the corresponding timestamp are stored in a score database (220, 221).

33. The method (100) of one of the preceding embodiments, when dependent on embodiment 3, wherein generating (151) the at least one further verbal statement (50) capable of provoking at least one further verbal response (51) from the user comprises selecting a question about the at least one contemporaneous feature (40).

34. The method (100) of one of the preceding embodiments, when dependent on embodiment 3, wherein obtaining (154) the at least one further verbal response (51) from the user via the audio interface (211) comprises obtaining the at least one further verbal response from the user in terms of a further timestamped audio waveform.

35. The method (100) of embodiment 34, wherein the at least one further verbal response from the user is applied to a speech-to-text algorithm, thereby generating a verbal feature string inheriting a further timestamp from the further timestamped audio waveform.
36. The method (100) of one of the preceding embodiments, when dependent on embodiment 2, wherein the at least one verbal response (31) from the user is applied to a speech-to-text algorithm, thereby generating a verbal feature string inheriting a further timestamp from the timestamped audio waveform.
37. The method (100) of embodiment 35 or 36, wherein determining (155) the at least one contemporaneous feature (40) of the creative work (10) based:
on the obtained at least one verbal response (31) from the user; or
on the obtained at least one further verbal response (51) from the user;
comprises applying the verbal feature string to a feature recognition algorithm configured to identify a noun that most likely relates to the at least one contemporaneous feature of the creative work.
38. The method (100) of embodiment 37, wherein identifying the at least one contemporaneous feature (40) of the creative work (10) comprises:
applying a text split algorithm configured to break the verbal feature string into one or more subunits each comprising sentences, phrases, clauses, and/or words; and
applying a noun extraction algorithm configured to perform a look-up for one or more subunits in a generic dictionary providing the at least one noun for the at least one contemporaneous feature of the creative work; and
thereby identifying the noun that most likely relates to the at least one contemporaneous feature of the creative work.
39. The method (100) of embodiment 37 or 38, wherein the feature recognition algorithm comprises at least one pre-trained machine learning algorithm.
40. The method (100) of one of the embodiments 37 to 39, wherein the noun that most likely relates to the at least one contemporaneous feature (40) of the creative work (10) inherits the further timestamp of the verbal feature string.
41. The method (100) of one of the embodiments 37 to 40, when dependent on embodiment 32, wherein the at least one contemporaneous feature (40) of the creative work (10), the noun that most likely relates to the at least one contemporaneous feature of the creative work and the further timestamp.
42. The method (100) of one of the preceding embodiments, when dependent on embodiment 2 or 3, further comprising generating (160) at least one tailored response (60) based on the cognitive load (20) and/or the corresponding contemporaneous feature (40).
43. The method (100) of embodiment 42, wherein generating (160) the at least one tailored response (60) is triggered by a request of a user or of a further individual, or automatically when the cognitive load (20) exceeds a predetermined cognitive load threshold.
44. The method (100) of embodiment 42 or 43, further comprising generating (161) at least one further tailored response (60) based on at least one cognitive load (20) and/or the at least one corresponding contemporaneous feature (40) queried from the score database (220, 221),
45. The method (100) of embodiment 44, wherein querying at least one cognitive load (20) and/or the at least one corresponding contemporaneous feature (40) can be subject to one or more conditions comprising:
a condition restricting stored timestamps; and
a condition restricting stored cognitive loads; and
a condition restricting stored contemporaneous features.
46. The method (100) of one of the embodiments 42 to 45, wherein the at least one tailored response (60) is based on a tailored response template (61).
47. The method (100) of embodiment 46, wherein the tailored response template (61) is a parametrizable text.
48. The method (100) of embodiment 46 or 47, wherein generating (160, 161) the at least one tailored response (60) based on the cognitive load (20) and the corresponding contemporaneous feature (40) comprises applying a tailored response algorithm configured to integrate at least one cognitive load, the at least one corresponding contemporaneous feature, and/or at least one corresponding timestamp into the tailored response template (61).
49. The method (100) of one of the preceding embodiments wherein a verbal statement comprises a name of the user.
50. The method (100) of one of the embodiments 42 to 49, comprising outputting (170) the at least one tailored response via a user interface (210) to the user.
51. The method (100) of one of the embodiments 42 to 50, wherein the at least one generated tailored response (60) is capable of provoking a third response (62) from the user, and the method further comprises:
prompting the user to vocally interact with the creative work system (200) by vocalizing the at least one generated tailored response (60); and
obtaining the third response (62) from the user via the user interface (210); and
executing a third response algorithm based on the third response (62) from the user, if the third response (62) from the user is recognized to be affirmative.
52. A creative work system (200) for measuring cognitive load (20) of a user creating a creative work (10) comprising:
a user interface (210) comprising an audio interface (211);
wherein the creative work system is configured to run the method (100) of one of the preceding embodiments.
53. The creative work system (200) of embodiment 52, wherein the audio interface (211) comprises at least one microphone (212) and at least one speaker (213).
54. The creative work system (200) of embodiment 52 or 53, comprising access to at least one database (220) via a communication channel (222).
55. The creative work system (200) of one of the embodiments 52 to 54, comprising a camera (230) configured to record at least one image or a sequence of images of the creative work (10) as creation progresses.
56. The creative work system (200) of one of the embodiments 52 to 55, wherein the user interface (210) comprises a graphical interface (214).

REFERENCE NUMERALS 10 creative work
20 cognitive load
30 verbal statement capable of provoking at least one verbal response from the user
31 verbal response from the user 31 predicted verbal response
32 contemporaneous feature
40 further verbal statement capable of provoking at least one further verbal response from the user
51 further verbal response from the user
60 (further) tailored response
61 a tailored response template
62 third response
100 computer-implemented method for measuring cognitive load of a user creating a creative work in a creative work system
110 generating at least one verbal statement capable of provoking at least one verbal response from the user
120 prompting the user to vocally interact with the creative work system
121 vocalizing the at least one generated verbal statement to the user via an audio interface of the creative work system
130 obtaining the at least one verbal response from the user via the audio interface
140 determining the cognitive load of the user based on the at least one verbal response obtained from the user
150 determining at least one contemporaneous feature of the creative work based on the at least one obtained verbal response from the user
151 generating at least one further verbal statement capable of provoking at least one further verbal response from the user
152 prompting the user to vocally interact with the creative work system
153 vocalizing the at least one generated further verbal statement to the user via an audio interface of the creative work system
154 obtaining at least one further verbal response from the user via the audio interface
155 determining at least one contemporaneous feature of the creative work based on the at least one obtained further verbal response from the user
160 generating at least one tailored response based on the cognitive load and/or the corresponding contemporaneous feature
161 generating at least one further tailored response based on at least one cognitive load and/or the at least one corresponding contemporaneous feature queried from the score database
170 outputting the at least one tailored response via a user interface to the user
180 feeding-back information related to the at least one cognitive load and/or the at least one corresponding contemporaneous feature via the user interface
200 creative work system
210 user interface
211 audio interface
212 microphone
213 speaker
214 graphical interface
220 database, candidate primitive database, response database, score database, tailored response template database
221 score database
222 communication channel
230 camera

The invention claimed is:

1. A computer-implemented method for measuring cognitive load of a user creating a creative work in a creative work system, comprising:

generating at least one verbal statement capable of provoking at least one verbal response from the user by:
applying a candidate verbal statement algorithm configured to generate one or more candidate verbal statements;
applying a conversation algorithm configured to generate for each candidate verbal statement one or more predicted verbal responses and corresponding one or more response probabilities, thereby generating, for each candidate verbal statement, a list of predicted verbal responses and a vector of response probabilities RPV;
applying a predicted verbal response assessment algorithm configured to assign a response score to each predicted verbal response, thereby generating, for each candidate verbal statement, a vector of response scores; and
applying a verbal response selection algorithm configured to select one of the one or more candidate verbal statements based on the one or more vectors of response probabilities and on the one or more vectors of response scores, thereby generating the at least one verbal statement based on the at least one predicted verbal response suitable for determining the cognitive load of the user;
prompting the user to vocally interact with the creative work system by vocalizing the at least one generated verbal statement to the user via an audio interface of the creative work system;
obtaining the at least one verbal response from the user via the audio interface; and
determining the cognitive load of the user based on the at least one verbal response obtained from the user.

2. The computer-implemented method of claim 1, wherein assigning the response score to each predicted verbal response comprises checking for one or more verbal features in each predicted verbal response and computing a feature score for each of the one or more verbal features.

3. The computer-implemented method of claim 2, wherein the one or more verbal feature comprises a verbal feature of a first type comprising:
a variety of phoneme use;
a variety of pseudo-syllable use; or
a response length.

4. The computer-implemented method of claim 3, wherein checking for the one or more verbal features in each predicted verbal response and computing the feature score for each of the one or more verbal features comprises applying each predicted verbal response to a phoneme use algorithm configured for:
identifying at least one phoneme of the predicted verbal response based on a predetermined list of phonemes;
counting the phonemes of the predicted verbal response;
counting unique phonemes of the predicted verbal response; and
dividing the count of the unique phonemes of the predicted verbal response by the count of the phonemes of the predicted verbal response, thereby computing a phoneme score, thereby computing the verbal feature score.

5. The computer-implemented method of claim 2, wherein assigning the response score to each predicted verbal response is based on at least one verbal feature score corresponding to at least one verbal feature of the predicted verbal response.

6. The computer-implemented method of claim 1, wherein selecting one of the one or more candidate verbal statements based on the one or more vectors of response probabilities and on the one or more vectors of response scores comprises:

multiplying, for each candidate verbal statement, the vector of response probabilities RPV and the vector of response scores, thereby generating, for each candidate verbal statement, a vector of weighted response scores;

summing, for each candidate verbal statement, components of the vector of weighted response scores, thereby generating, for each candidate verbal statement, a total selection score; and selecting one of the one or more candidate verbal statements with a highest total selection score.

7. The computer-implemented method of claim 1, wherein determining the cognitive load of the user based on the at least one verbal response obtained from the user comprises assessing at least one vocal feature of the at least one verbal response obtained from the user.

8. The computer-implemented method of claim 7, wherein determining the cognitive load of the user based on the at least one verbal response obtained from the user comprises applying one or more cognitive load feature assessment algorithms, wherein each cognitive load feature assessment algorithm corresponds to a vocal feature and is configured for:

generating a vocal feature vector representation of the corresponding vocal feature for the at least one verbal response from the user, thereby generating one or more vocal feature vector representations.

9. The computer-implemented method of claim 8, wherein determining the cognitive load of the user based on the at least one verbal response obtained from the user comprises applying the one or more vocal feature vector representations to a cognitive load score algorithm configured for:

comparing each of the one or more vocal feature vector representations to at least one predetermined benchmark for cognitive load, wherein each comparison comprises computing a predetermined criterion based on at least one vocal feature vector representation and the at least one predetermined benchmark for cognitive load;

counting the one or more vocal feature vector representations satisfying a corresponding predetermined criteria;

counting the one or more vocal feature vector representations; and dividing a count of the one or more vocal feature vector representations satisfying the corresponding predetermined criteria by a count of the one or more vocal feature vector representations, thereby determining the cognitive load of the user.

10. The computer-implemented method of claim 1, further comprising:

determining at least one contemporaneous feature of the creative work based on the at least one obtained verbal response from the user, wherein the at least one verbal response from the user is applied to a speech-to-text algorithm, thereby generating a verbal feature string inheriting a further timestamp from a timestamped audio waveform.

11. The computer-implemented method of claim 10, wherein determining the at least one contemporaneous feature of the creative work is based on the obtained at least one verbal response from the user or on an obtained at least one further verbal response from the user, and further comprising:

applying the verbal feature string to a feature recognition algorithm configured to identify a noun that most likely relates to the at least one contemporaneous feature of the creative work.

12. The computer-implemented method of claim 10, further comprising:

generating at least one tailored response based on the cognitive load and/or corresponding contemporaneous feature.

13. The computer-implemented method of claim 12, wherein the at least one tailored response is based on a tailored response template.

14. The computer-implemented method of claim 1, wherein the creative work comprises a visual artwork.

15. The computer-implemented method of claim 14, wherein the visual artwork comprises one or more of a drawing, a painting, a calligraphy, or a sculpture.

16. A system for measuring cognitive load of a user creating a creative work in a creative work system, comprising at least one non-transitory computer readable medium storing instructions which, when executed by one or more processors, cause the one or more processors to perform operations comprising:

generating at least one verbal statement capable of provoking at least one verbal response from the user by:

applying a candidate verbal statement algorithm configured to generate one or more candidate verbal statements;

applying a conversation algorithm configured to generate for each candidate verbal statement one or more predicted verbal responses and corresponding one or more response probabilities, thereby generating, for each candidate verbal statement, a list of predicted verbal responses and a vector of response probabilities RPV;

applying a predicted verbal response assessment algorithm configured to assign a response score to each predicted verbal response, thereby generating, for each candidate verbal statement, a vector of response scores; and applying a verbal response selection algorithm configured to select one of the one or more candidate verbal statements based on the one or more vectors of response probabilities and on the one or more vectors of response scores, thereby generating the at least one verbal statement based on the at least one predicted verbal response suitable for determining the cognitive load of the user;

prompting the user to vocally interact with the creative work system by vocalizing the at least one generated verbal statement to the user via an audio interface of the creative work system;

obtaining the at least one verbal response from the user via the audio interface; and determining the cognitive load of the user based on the at least one verbal response obtained from the user.

17. The system of claim 16, wherein assigning the response score to each predicted verbal response comprises checking for one or more verbal features in each predicted verbal response and computing a feature score for each of the one or more verbal features.

18. The system of claim 17, wherein the one or more verbal features comprises a verbal feature of a first type comprising:

a variety of phoneme use;
a variety of pseudo-syllable use; or
a response length.

19. The system of claim 18, wherein checking for the one or more verbal features in each predicted verbal response and computing the feature score for each of the one or more verbal features comprises applying each predicted verbal response to a phoneme use algorithm configured for:
- identifying at least one phoneme of the predicted verbal response based on a predetermined list of phonemes;
- counting the phonemes of the predicted verbal response;
- counting unique phonemes of the predicted verbal response; and
- dividing the count of unique phonemes of the predicted verbal response by the count of the phonemes of the predicted verbal response, thereby computing a phoneme score, thereby computing the verbal feature score.

20. An apparatus comprising:
at least one processor; and
at least one memory including computer program code for one or more programs,
the at least one memory and the computer program code configured to, with the at least one processor, cause the apparatus to perform at least the following,
generate at least one verbal statement capable of provoking at least one verbal response from a user by:
- apply a candidate verbal statement algorithm configured to generate one or more candidate verbal statements;
- apply a conversation algorithm configured to generate for each candidate verbal statement one or more predicted verbal responses and corresponding one or more response probabilities, thereby generating, for each candidate verbal statement, a list of predicted verbal responses and a vector of response probabilities RPV;
- apply a predicted verbal response assessment algorithm configured to assign a response score to each predicted verbal response, thereby generating, for each candidate verbal statement, a vector of response scores; and
- apply a verbal response selection algorithm configured to select one of the one or more candidate verbal statements based on the one or more vectors of response probabilities and on the one or more vectors of response scores, thereby generating the at least one verbal statement based on the at least one predicted verbal response suitable for determining a cognitive load of the user;

prompt the user to vocally interact with a creative work system by vocalizing the at least one generated verbal statement to the user via an audio interface of the creative work system;
obtain the at least one verbal response from the user via the audio interface; and
determine a cognitive load of the user based on the at least one verbal response obtained from the user.

* * * * *